United States Patent [19]

Richardson

[11] 4,144,131

[45] Mar. 13, 1979

[54] IMMOBILIZATION OF ENZYMES ON HUMAN TISSUE OR ERYTHROCYTES

[75] Inventor: Thomas Richardson, Madison, Wis.

[73] Assignee: Wisconsin Alumni Research Foundation, Madison, Wis.

[21] Appl. No.: 472,588

[22] Filed: May 23, 1974

[51] Int. Cl.² ............................................. C07G 7/02
[52] U.S. Cl. ........................................ 195/68; 195/63; 195/DIG. 11; 424/94
[58] Field of Search .................. 195/63, 68, DIG. 11; 424/94; 260/112 R

[56] References Cited

U.S. PATENT DOCUMENTS

| | | | |
|---|---|---|---|
| 3,639,558 | 2/1972 | Csizmas et al. | 195/68 X |
| 3,654,083 | 4/1972 | Moelker | 195/68 X |
| 3,691,016 | 9/1972 | Patel | 195/68 |
| 3,806,417 | 4/1974 | Beaucamp et al. | 195/63 |
| 3,843,447 | 10/1974 | Burkoth | 195/68 |

*Primary Examiner*—David M. Naff
*Attorney, Agent, or Firm*—McDougall, Hersh & Scott

[57] ABSTRACT

Enzymes and macromolecules are immobilized in vivo or in vitro on human tissue or erythrocytes by the reaction of the enzyme with a coupling agent to form an enzyme derivative containing electrophilic groups and reacting the enzyme derivative with the tissue or erythrocyte containing a sulfhydryl group or other nucleophilic group.

8 Claims, No Drawings

IMMOBILIZATION OF ENZYMES ON HUMAN TISSUE OR ERYTHROCYTES

The invention described herein was made in the course of work under a grant or award from the Department of Health, Education, and Welfare.

This invention relates to the immobilization of enzymes and it relates more particularly to the immobilization of enzymes on human erythrocytes to retard their elimination and/or to enhance their biological activity.

Therapy by the use of enzymes has found widespread acceptance in the treatment of various diseases. L-asparaginase has been shown to be useful in the treatment of acute lymphoblastic leukemia, leukemic lymphosarcoma and lymphosarcoma (D. Crowther, L-asparaginase and Human Malignant Disease, Nature 229, 168 (1971)). Two properties of L-asparaginase favor its use in leukemia therapy, namely: (1) it successfully induces remission in some patients with acute lymphocytic leukemia in relapse, and (2) there is no cross resistance with other oncolytic drugs (Asparaginase in Combination Chemotherapy for Remission Induction of Childhood Acute Lymphocytic Leukemia, C. B. Pratt, D. Roberts, E. Shanks, K. L. Warmath, and R. Jackson, Cancer Res. 33, 2020 (1973)).

The success that has been experienced with L-asparaginase has stimulated the investigation of other enzymes with anti-tumor activity (T. Oki, M. Shirai, T. Yammamoto and K. Soda, Febs. Lett. 33, 286–8 (1973)). In addition, there are a wide variety of genetic deficiency diseases characterized by defective or absent enzymes, which may respond to enzyme therapy (W. E. C. Wacker and T. L. Coombs, Clinical Biochemistry, Ann. Rev. Biochem. 38, 539–68 (1971). R. O. Brady, J. F. Tallman, W. G. Johnson, A. E. Gail, W. R. Leahy, J. M. Quirk and A. S. Dekaban, N. Engl. J. Med. 289, 9–14, 1973, described the treatment of Fabry's disease with purified placental ceramidetrihexosidase, resulting in a transitory decrease in plasma ceramidetrihexoside.

The difficulties experienced with enzyme therapy include the antigenicity of enzymes and their relatively short biological half lives. Factors that limit treatment of leukemia as, for example, with L-asparaginase, are (1) the development of resistance by leukemia cells; (2) the immunologic response of the host against L-asparaginase, or (3) the relatively short biological half life of L-asparaginase. In patients, the plasma half life of *Escherichia coli* L-asparaginase ranges from 8–30 hours, depending upon the variation among subjects as well as the source of the enzyme. Furthermore, the development of antibodies against L-asparaginase may not only lead to anaphylactic shock, but also to a decrease in the biological half life of the enzyme. For example, in sensitized mice bearing a lymphoma, no L-asparaginase was detectable in the circulation from 2 minutes to 24 hours after IV administration, wheras the biological half life of the enzyme in unsensitized mice was 7½ hours (1).

In addition to the inherent biological effects of L-asparaginase, successful treatment may depend upon minimizing the immunosuppressive effects of the enzyme. L-asparaginase has been shown to possess marked immunosuppressive activity. Presumably the powerful immunosuppression by L-asparaginase antagonizes immunological tumor inhibition.

Such short half lives of exogenous enzymes, coupled with the limited availability of homologous human enzymes introduce limitations in enzyme therapy. Brady et al, supra, induced the reduction of serum ceramidetrihexoside in patients with Fabry's disease by IV administration of purified ceramidetrihexoside from human placenta. However, the enzyme was rapidly removed from the circulation by the liver within one hour and the abnormally high ceramidetrihexoside levels returned within 48 hours.

Efforts have been made to increase the biological half life of such enzymes and to modify their immunologic and immunosuppressive response of the host. Some investigators have suggested that immunologic and immunosuppressive effects of L-asparaginase might be minimized by giving intermittent large dosages of enzyme rather than repeated small doses.

Attemps to increase the effectiveness and biological half life of L-asparaginase include the preparation of soluble and immobilized derivatives. The biological half lives of various soluble L-asparaginase derivatives have been shown to increase with increased isoelectric point (2) and this relationship was associated with enhanced therapeutic effectiveness in leukemic mice. Other soluble derivatives that have been shown to possess increased half lives include partially deamidated L-asparaginase (3), partially amidated L-asparaginase (4), partially amidonated L-asparaginase (5), partially acylated L-asparaginase (6) and azo L-asparaginase (7).

In addition, immobilized derivatives of L-asparaginase have been prepared with the intent of obviating the immunologic and half life shortcomings of the enzyme. L-asparaginase has been immobilized on a Dacron vascular prosthesis and implanted in the abdominal aorta of a dog (8). After 7 days in vivo, 44.5% of the initial activity of the graft remained. The disadvantage of using this technique is that it requires major surgery.

Other suggested modes of therapy include the immobilization of L-asparaginase in columns (9) or in nylon tubing (10) to be used as extracorporeal shunts in depleting blood L-asparagine, with the variation of hemodialysis against L-asparaginase. The disadvantages of these techniques is the requirement for immobilization of the patient, the requirement for intermittent treatment, and the danger of thrombosis and infection.

One of the more promising means for immobilization in vivo is the encapsulation of the enzyme in microcapsules (11) or a polyacrylamide gel (12) and injection into the peritoneal cavity. This system increases the biological half life of L-asparaginase and is more effective than soluble L-asparaginase in retarding the development of implanted lymphosarcoma in mice (13). A disadvantage is that the substrate must permeate the walls of the microcapsule. To prevent complications, the encapsulated material should be biodegradable and this would cause the released enzyme to be immunogenic and toxic.

It is an object of this invention to increase the biological half lives of enzymes and improve upon their immunogenicity and toxicity by immobilization of the enzymes in vivo or in vitro on tissue or human erythrocytes.

More specifically, it is an object of this invention to provide enxyme derivatives capable of being reacted with tissue or human erythrocyte nucleophiles to become immobilized on the tissue or erythrocyte and it is a related object to provide enzyme derivatives which are reactive with tissue functional groups so as to become interbonded therewith.

In accordance with the practice of this invention, immobilization of the enzyme is achieved by first forming a derivative of the enzyme to provide the enzyme with reactive groups which react with groups in the human tissue or erythrocytes whereby the enzyme derivative becomes immobilized on the tissue or erythrocyte, as by an interbonded relationship therebetween.

While the invention will be described with reference to the immobilization of enzymes such as L-asparaginase and alpha-amylase, it will be understood that the invention is applicable to the immobilization of other enzymes such as phenylalanine ammonia lyase, glutaminase, lecithin cholesterol acyl transferase, and lipoprotein lipase. It will be further understood that immobilization of enzymes other than for clinical use is intended to be included within the invention, such as the immobilization of enzymes on yeast cells, immobilization of enzymes on microbial cells, which enables the microorganism to attack substrates, such as amylase, that the organism could not itself attack. The concepts of this invention have application also to the immobilization of materials other than enzymes such as macromolecules represented by antigens, viruses, proteins, hormones, antibodies, and proteins such as sommatotrophins (growth), gonadotrophins (sexual activity) and other pituitary hormones.

Characteristic of enzymes (including macromolecules and proteins) with which the invention may be practiced, are the presence of nucleophilic groups or carboxyl groups which allow derivatization with a coupling compound that yields a derivative containing electrophilic groups that will enable the desired interbonded relationship to be established with nucleophilic or other groupings present in the tissue or human erythrocytes for immobilixation of the enzyme thereon. Electrophilic groups are defined in the context of this invention as any chemical grouping which will react with nucleophiles to form a stable covalent bond.

As generally described, the tissue or human erythrocyte on which the enzyme is immobilized is relied upon to contain one or more nucleophilic groups such as sulfhydryl groups, amino groups, imidazole groups, carboxylato groups, tyrosine anionic groups and the like. The coupling which is engaged in bringing about the interbonded relationship with the enzyme derivative will determine the type of electrophilic group required to be provided in the enzyme derivative, which in turn will influence the coupling compound with which the derivative is formed.

Broadly defined, derivatization of the enzyme is restricted to a coupling compound containing an electrophilic group that will react with nucleophiles on the tissue or erythrocyte to form the interbonded relationship. Representative of these electrophilic groups are $\alpha$, $\beta$ unsaturated carbonyls, alkyl halides and thiol reagents such as substituted maleimides. In addition, the coupling compound can be coupled to the enzyme via one or more of the functional groups in the enzyme such as amino, carboxyl and tryosine groups. For this purpose coupling compounds should contain free carboxyl groups, free amino groups, aromatic amino groups, and other groups capable of reaction with enzyme functional groups. Highly charged derivatives of enzymes can also be prepared for immobilization on tissues or erythrocytes through electrostatic bonding. Examples of these derivatives would include polylysyl and polyglutamyl enzymes. In the text entitled "Chemical Modification of Proteins," authored by G. E. Means and R. E. Feeney, 1971, and published by Holden Day, Inc. of San Francisco, Ca., description is made of compounds capable of being coupled with proteins but they still retain their electrophilcity. More specifically, the same compounds, though limited to compounds containing electrophilic groups to form the bridge between enzyme derivative and tissue or erythrocyte, can be used in the practice of this invention for achieving the desired derivative formation of the enzymes (macromolecules or proteins), for use in the practice of this invention.

The choice of the reactive group embodied in the enzyme derivative depends on the reactive conditions employed to couple the electrophile with the nucleophilic groups of the tissue or erythrocyte for immobilization. A controlling factor is the desire not to inactivate the coupling agent prior to coupling of the enzyme immobilized by the attachment of the enzyme to the tissue or human erythrocyte.

Such coupling immobilization reactions can proceed in a number of ways:

Typically, a coupling agent can be used to form a bridge between the macromolecule and the erythrocyte or tissue. In this case, the coupling agent should possess a functional group such as a carboxyl group which can be caused to react with the enzyme.

One pathway for preparing the reactive enzyme or macromolecular derivative comprises the utilization of carboxyl groups in the coupling agent to form mixed anhydrides which react with the enzyme or macromolecule, in which use is made of an activator which is capable of forming the mixed anhydride. Representative of such activators are isobutylchloroformate or other chloroformates which give a mixed anhydride with coupling agents such as 5,5'-(dithiobis (2-nitrobenzoic acid) (DTNB), p-chloromercuribenzoate (CMB), or m-maleimidobenzoic acid (MBA). The mixed anhydride of the coupling agent reacts with the enzyme or macromolecule to yield the reactive derivative which in turn can react with nucleophilic groups on the tissue or erythrocyte to immobilize the macromolecule. Examples of other activators include carbodiimides or isoxazolium salts.

Instead, functional groups on the enzyme such as carboxyl groups can be activated with carbodiimides and the like activators. Subsequently, functional groups on the bridging reagent, such as amino groups, will react with the activated group on the enzyme to form the reactive enzyme derivative. In addition, the coupling agent should possess a second reactive grouping which will react with appropriate nucleophilic groups on the tissue or erythrocyte to form the bridge. Typical of such reactive groupings as described in the book by Means and Feeney, supra are alkylating agents such as iodoacetic acid, $\alpha$, $\beta$ unsaturated carbonyl compounds, such as acrylic acid and the like, thiol reagents, such as mercurials, substituted maleimides and the like.

Alternatively, functional groups on the enzyme can be activated so as to react directly with nucleophiles on erythrocytes and tissues to obviate the need for a bridgeforming compound. For this purpose, beneficial use is made of an activator such as Woodward's Reagent K or the like reagent which brings about the formation of carboxyl groups in the enzyme into enol esters, as distinguished from mixed anhydrides. The enol ester derivatives of enzymes will subsequently react with nucleophilic groups on the tissue or erythrocyte to effect immobilization of the macromolecule.

The activators function in the above manner to help form an interbonded relationship between macromolecule and tissue or erythrocyte, but they are not significant in the coupling reaction itself.

Having described the basic concepts of this invention, examples will now be made, by way of illustration but not by way of limitation, of the derivatization of enzymes and coupling to tissue or human erythrocyte, representative of the pathways heretofore described.

EXAMPLE I

Mixed Anhydrides

A. Para-mercuribenzoate (PMB) (coupler), triethylamine and isobutylchloroformate (activator) were dissolved in anhydrous dioxane in equimolar ratios at 1° C. The mixed anhydride forms in about 20 minutes.

The dioxane solution of the mixed anhydride was added to an equal volume of alpha-amylase solution in water at pH 9.5–10.0 and the reaction was allowed to proceed for four hours at 4° C.

B. A control enzyme solution was prepared as described above except that the activator isobutylchloroformate was omitted.

At the conclusion of the reactions, the enzyme mixtures A and B were dialyzed exhaustively against tap water and then against isotonic saline solution maintained at pH 7.4 with 0.1 M phosphate. The enzyme mixtures were then centrifuged at 1000 × G for a total of 45 minutes to remove suspended material.

Erythrocytes were isolated by centrifugation of fresh, normal, human whole blood samples of mixed types. The packed erythrocytes were resuspended and washed four times with isotonic saline. The red cells were then suspended in isotonic solutions of PMB enzyme A or control enzyme B, containing 9 units/ml of activity, and the systems were gently shaken for 10 minutes at 28 cycles per minute. The treated erythrocytes were washed five times with isotonic saline and then subjected to analysis for alpha-amylase activity.

Enzyme activity was measured by the reduction of starch-iodine color and was defined as follows (14):

$$1 \text{ unit} = \frac{A_o - A}{A_o} \times N \text{ in 3 ml}$$

starch solution pH 7.4 at 37° C. where $A_o$ is absorbancy at zero time
$A$ is absorbancy at 10 min.
$N$ is dilution factor of enzyme Alpha-amylase activity was measured on the erythrocytes by resuspending the washed cells in 3 ml of isotonic starch solution and shaking for one hour in a water bath at 37° C. and at 150 cycles per minute. The percentage of enzyme activity retained on the erythrocytes after one hour incubation was measured by washing the cells, as before, two times and resuspending the erythrocytes in 3 ml isotonic starch solution to determine the activity. The enzymatic response, at the level occurring on the red cells, was linear over a two-hour period. The amount of enzyme released into the supernatant was measured after a period of incubation for an additional hour, as described above.

Osmotic hemolysis, hematocrit and mechanical fragility of treated and control erythrocytes was determined by the method outlined by Dacie and Lewis in "Practical Haematology," 4th Edition, 1966, published by J. and A. Churchill, Ltd., London. The mechanical fragility was determined both by shaking the erythrocytes under conditions similar to the enzyme treatment and in the presence of glass beads. The erythrocytes were counted by the improved Neubauer method.

Mercury contents of the enzyme solutions as well as those of the erythrocytes were determined by flameless atomic absorption. Protein concentrations were measured by the methods of Lowry et al., J. Biol. Chem. 193, 265–275 (1951), using bovine serum albumin as a standard.

TABLE I.

Mercury contents and specific activities of alpha-amylase enzymes.

|  | ug mercury/ug protein | activity (units/ml) |
|---|---|---|
| PMB-alpha-amylase | 0.079 – 0.173 | 7.55 – 9.02 |
| Control alpha-amylase | 0.011 – 0.024 | 8.95 |

TABLE II.

Characteristics of human erythrocytes after incubation with enzyme solutions.

|  | PMB-alpha-amylase | Control alpha-amylase |
|---|---|---|
| Gram atoms Hg/cell | $4.11 - 4.23 \times 10^{-17}$ | $3.48 - 3.80 \times 10^{-17}$ |
| Units alpha-amylase/cell | $8.89 \pm 1.34 \times 10^{-11}$ | 0.0 |

As shown in TABLE I, the PMB-alpha-amylase contains 0.079–0.173 micrograms of mercury per microgram of protein. Assuming a molecular weight of 48,000 for the alpha-amylase, this would amount to 19–40 gram atoms of mercury per mole of enzyme. By comparison, the control enzyme contains 0.011–0.024 micrograms of mercury per microgram protein, which would represent 3–6 gram atoms of mercury per mole of enzyme. Apparently, free PMB binds to the enzyme in the absence of the coupling agent.

As shown in TABLE II, the enzymatic activity per cell was $8.89 \times 10^{-11}$ units whereas control and untreated cells contained no activity.

When the cells were shaken for one hour, 24.9% ± 1.8 of the amylase activity was lost to the supernatant whereas 57.2% ±2.8 of the activity was retained on the cells.

As indicated in the following TABLE III, the mechanical fragility of erythrocytes, shaken under similar conditions, was only 1–1.3% compared to 2.6–5.8% for untreated cells. Thus, it is unlikely that significant amounts of the supernatant activity resulted from cellular disintegration.

TABLE III shows that the immobilization of PMB-alpha-amylase on human erythrocytes has only a limited effect on the physical properties of the cells. The mechanical fragility in the presence and absence of glass beads was actually less than untreated cells, indicating increased membrane stability to mechanical damage. Hematocrits for treated, control and untreated cells were essentially the same, indicating little change in the shape of the cells. The osmotic hemolysis of the PMB-alpha-amylase treated and control cells fell within the normal range for human erythrocytes.

TABLE III.

Properties of human erythrocytes treated with PMB-A-amylase.

|  | PMB-A-amylase | Untreated cells |
|---|---|---|
| Mechanical fragility[1] | 1.15 ± % 0.15 | 4.2 ± % 1.6 |
| Mechanical fragility[2] | 7.75 ± 0.0 | 15.9 ± 0.1 |

TABLE III.-continued

| | Properties of human erythrocytes treated with PMB-A-amylase. | |
|---|---|---|
| | PMB-A-amylase | Untreated cells |
| Hematocrit[3] | 46.5 | 46 |

[1]Shaken under same conditions as cells treated with PMB-A-amylase. Values are averages from two experiments ± deviation from the mean. Analyses in duplicate.
[2]Shaken in the presence of 3 glass beads each 4 mm in diameter. Values are averages from two experiments ± deviation from the mean. Analyses in duplicate.
[3]Hematocrit of cells incubated with control enzyme solution was 46.5%. Values are means of two replicates.

EXAMPLE II

Mixed Anhydrides 5, 5'-dithiobis (2-nitrobenzoic acid) (DTNB) triethylamine and isobutychloroformate were dissolved in anhydrous dioxane in equimolar proportions at 1° C.

The dioxane solution of the formed mixed anhydride was added to an equal volume of enzyme solution in water at pH 9.5–10.9, after 0.05 mM of 4. chloro-3-maleimide benzoic acid had been added to the enzyme solution to block any extraneous sulfhydryl groups. The reaction was allowed to proceed for about four hours at 4° C. In this case, the reaction between the enzyme derivatives and erythrocytes was blocked with dithiothreitol indicating the formation of covalent linkage between enzyme and cell.

EXAMPLE III

As in EXAMPLE I, L-asparaginase is coupled with p-mercuribenzoate via its carboxyl group, using the mixed anhydride technique represented by the following equation:

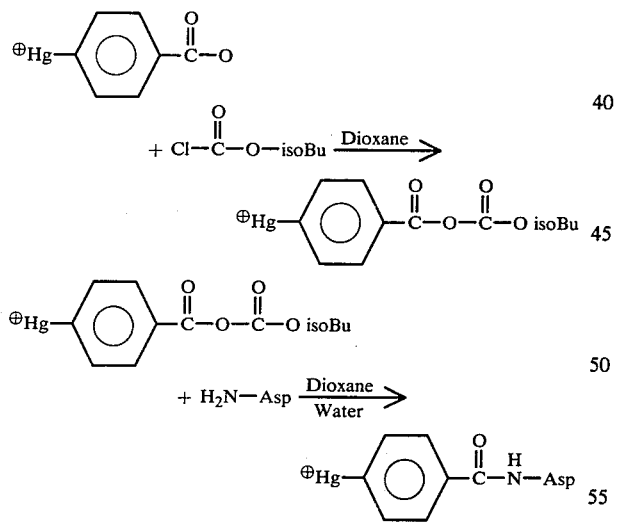

The procedure for the preparation of the derivative and for coupling onto the enzyme is the same as that described in EXAMPLE I with the exception that L-asparaginase is substituted for alpha-amylase.

EXAMPLE IV

This example couples L-asparaginase with 5, 5'-dithiobis (2-nitrobenzoic acid) to form the corresponding 5, 5'-dithiobis (2-nitrobenzoate)-L-asparaginase by the procedure described in EXAMPLE II except that DTNB is used as the coupling agent instead of para-mercuribenzoate. The reaction may be represented by the following equation:

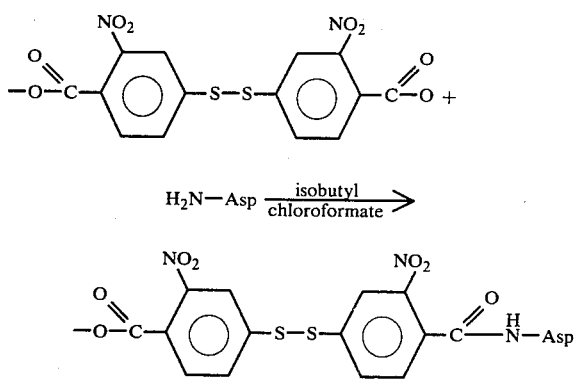

The reaction of the enzyme derivative of EXAMPLE IV with the thiol group of the tissue or erythrocyte may be represented by the following equation:

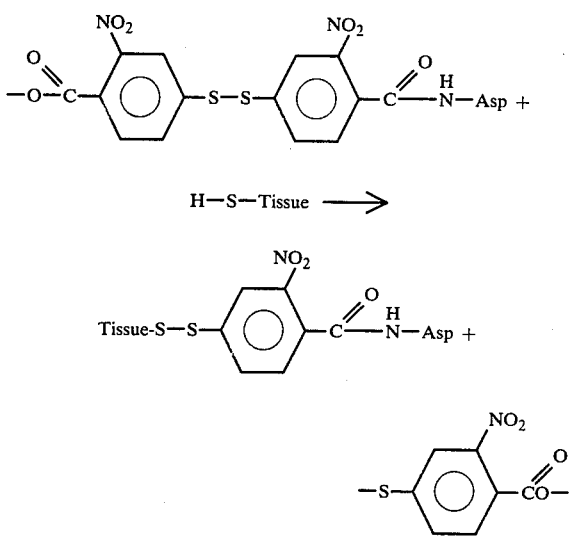

EXAMPLE V

This example illustrates the coupling of the enzyme with substituted maleimides such as M-maleimido benzoic acid and others of a wide variety of maleimide derivatives, using Woodward's Reagent K as the activator, representing the enol ester pathway.

m-Maleimido-benzoic acid is reacted in water-dioxane solution with L-asparaginase in the presence of Woodward's Reagent K, at about pH 5 to minimize alkaline hydrolysis of the maleimide. The reaction is represented by the following equation:

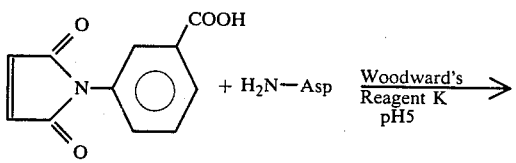

-continued

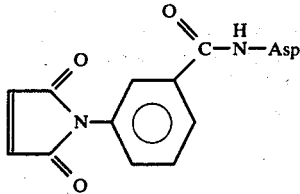

The formed enzyme derivative maleimido-L-asparaginase is immobilized upon reaction with tissue sulfhydryl groups at physiological pH, in accordance with the following equation:

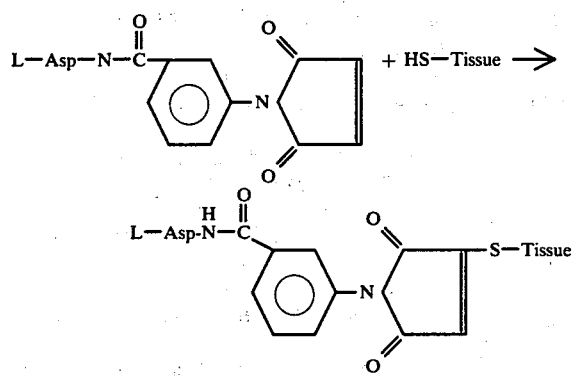

EXAMPLE VI

Other isoxazolium-enzyme adducts can be prepared as in EXAMPLE V by substitution with other enzymes such as trypsin or alpha-amylase and/or L-asparaginase as in EXAMPLE V.

The isoxazolium trypsin adduct reacts with nucleophiles of the erythrocytes to form trypsin derivatives whereby the protein carboxyl groups are modified.

This appears to be an ideal system with L-asparaginase when reacted in the presence of Woodward's Reagent K, which, upon subsequent injection, enables the product to react with tissue nucleophilic amino groups, the sequence of events being as follows:

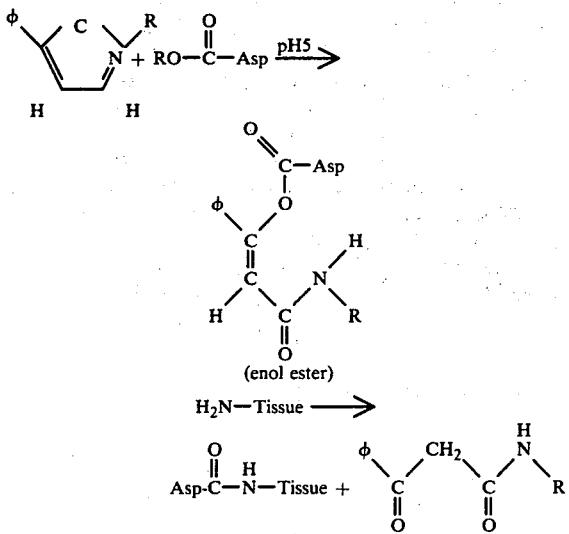

The reactive enol ester can be purified on Biogel 2-p and freeze dried. The stable freeze dried L-asparaginase adduct can be dissolved and injected for in vivo immobilization.

Activated vinyl compounds, represented by acrylic acid, acrylonitrile, methylacrylate and acrylamide react with nucleophiles (Nu:) by a Michael type addition as follows:

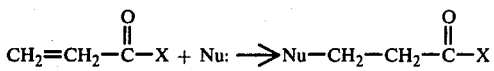

At pH 8 or above, the unprotonated amines react readily, whereas above pH 6.5 anionic sulfur becomes the primary nucleophile. However, the intrinsic rate of reaction of anionic sulfur is some 300 times faster than an unprotonated amine. Thus, acrylic derivatives of enzymes would react primarily with thiol groups under physiological conditions.

EXAMPLE VII

Acrylic acid is dissolved in water at pH 7.2 and cooled to 4° C. An equimolar quantity of Woodward's Reagent is dissolved in a small amount of water and added to the solution of acrylic acid and allowed to react for a few minutes.

The solution is added to a solution of enzyme, such as L-asparaginase, alpha-amylase, trypsin and the like, and allowed to react at 15 hours at 4° C.

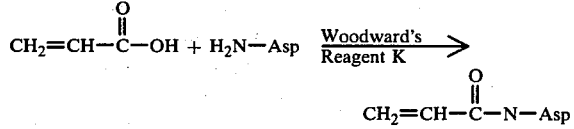

This derivative reacts with the tissue thiol groups to become immobilized in vivo via the double bond.

The following example illustrates the pathway for immobilization via the formation of enzyme derivatives by reaction with carbodiimides.

EXAMPLE VIII

A coupling reagent, such as DTNB or PMB of the type used in Examples I to IV, and enzyme (ether alpha-amylase or L-asparaginase) are dissolved in water-dioxane, at pH 4. A quantity of water soluble carbodiimide (1-cyclohexyl-3-)-2morpholino-ethyl) carbodiimide metho-p-toluene sulfonate (activator) equimolar to the amount of coupling agent is added and the reaction is allowed to proceed at pH 4 for 30 minutes at room temperature and overnight at 0° C.

Immobilization of the enzyme by coupling the derivatives of the foregoing Examples II to VIII onto tissue or erythrocytes via nucleophilic groups follows the procedure described in EXAMPLE I. Essentially it involves reacting the respective enzyme derivative in physiologically buffered saline solution with cells or with tissue for approximately 30 minutes at ambient temperature, preferably after purifying the enzyme derivative.

The derivatives from EXAMPLES I-VIII can be purified by passing the reaction mixture through Sephadex G-10 or by dialysis. Most of the enzyme derivatives can be freeze dried or concentrated by ultrafiltration.

EXAMPLE IX

Meta-maleimidobenzoic acid (0.05 mole) was coupled to 0.1 g of the lyophilized α-amylase, using the mixed anhydride technique of Erlanger, Borek, Beiser and Lieberman (1957) J. Biol. chem. 228, 713-727. Meta-maleimidobenzoic acid was treated with an equal molar ratio of isobutyl chloroformate and triethylamine in anhydrous dioxane, at 4° C. for 20 min. to prepare the mixed anhydride. The mixed anhydride was added to a suspension of α-amylase in anhydrous dioxane. The reaction proceeded for 6 hours at room temperature with the reaction vessels covered by Parafilm to prevent absorption of moisture.

At the conclusion of reaction, the enzyme mixture was washed 3 times each with 20 ml of anhydrous dioxane to remove excess meta-maleimidobenzoic acid. The enzyme mixture was dried in vacuo with the aid of a rotary evaporator. After drying, the enzyme was dissolved in 10 ml of phosphate buffer, 0.025 M, pH 6.5, and dialyzed against deionized water overnight, then lyophilized. Before coupling to the erythrocytes, 0.01 g of the dried enzyme was dissolved in 11 ml saline and centrifuged at 1,000 xg for 15 min to remove suspended, crosslinked enzyme. One milliliter of 0.1 M phosphate buffer was added to maintain the pH at 7.4. The control enzyme solutions contained all the reagents except the isobutyl chloroformate and were prepared as described above.

Erythrocytes were isolated by centrifugation of fresh, normal human whole blood samples of mixed types obtained from a local hospital. The packed erythrocytes were resuspended and washed 4 times with isotonic saline. The red blood cells were then suspended in the maleimidobenzoic acid-enzyme solution (244.1 ± 8.0 units/mg) and the maleimidobenzoic acid-enzyme solution plus cysteine hydrochloride (8.3 mM) and dithiolthreitol (4.2 mM) all at pH 7.4.

The systems were gently shaken on a wrist-action shaker for 1 hr at 28 cycles per minute. The treated erythrocytes were washed 6 times with isotonic saline and were then subjected to analysis for α-amylase activity [Chen and Richardson (1974) Parmacol. Res. Commun. (In press.)]. Enzyme activity on cells and the percentage of enzyme activity retained on the erythrocytes after an additional incubation of one hour at 37° C. were measured by the method of chen and Richardson, supra. Osmotic hemolysis, hematocrit and mechanical fragility of erythrocytes after treatment with maleimidoenzyme and the control were determined by the methods outlined by Dacie and Lewis (1968) Practical Haematology, 4th Ed., J. and A. Churchill Ltd., London. The erythrocytes were counted by the improved Neubauer method (Dacie and Lewis, supra). The maleimido contents of the enzymes were determined with an Acta III spectrophotometer, using 677 as the molar extinction coefficient for maleimidobenzoic acid at 300 nm. Untreated enzyme was used as a blank. From protein concentrations determined by the method of Lowry, Rosebrough, Farr and Randall (1951) J. Biol. Chem. 193, 265-275, it was possible to subtract the absorption of an equivalent amount of enzyme at 300 nm from that of the MBA-α-amylase conjugate. The increase in absorbance over the blank value was used to calculate the MBA content of the enzyme adduct.

The MBA-α-amylase conjugate reacts with cellular thiol groups as follows:

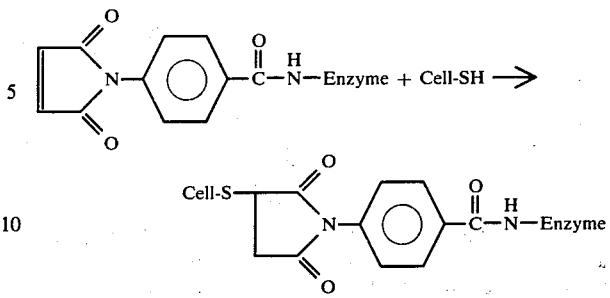

Sulfhydryl compounds such as those in cysteine or dithiothreitol should block the above reaction. Indeed, it was observed that preincubation of the MBA-α-amylase conjugate with cysteine (8.3mM) and dithiothreitol (4.2 mM) completely blocked the coupling of enzyme to the erythrocytes.

Spectral analysis of the MBA-α-amylase conjugates in the ultraviolet region (4 replicates from 2 preparations) indicated $10 \pm 0.5$ moles MBA per mole of enzyme whereas control enzyme preparations averaged $2.55 \pm 2.05$ moles MBA per mole of enzyme. A molecular weight of 48,000 was assumed for the α-amylase (Smolka, Birnbaum and Darnall (1971) Biochemistry 10, 4556–4561).

Analyses of 15 replicates, using 2 enzyme preparations, indicated enzymic activity retained on erythrocytes treated with MBA -α-amylase was $2.72 \pm 0.44 \times 10^{-10}$ unit/cell. This value is slightly higher than the $2.10 \pm 0.64 \times 10^{-10}$ unit/cell observed for the 5,5'dithiobis (2 nitrobenzoid acid) (DTNB) adduct of α-amylase (Chen and Richardson (1974a) Pharmacol. Res. Commun.) (in press). Erythrocytes treated with control enzyme solutions exhibited no detectable activity. Furthermore, coupling of the enzyme derivative to erythrocytes was blocked by L-cysteine and dithiothreitol indicating covalent addition of thiol to the maleimide residue.

After the initial incubation, the treated erythrocytes were spun down and resuspended in buffered, isotonic substrate to measure residual enzyme activity on the cells. Analyses of 9 replicates from 3 enzyme preparations indicated $79.2 \pm 17.9\%$ of the original activity remained on the erythrocytes. This retention of activity was substantially higher than that for DTNB-α-amylase (Chen and Richardson, 1974a, supra) indicating greater stability of the covalent linkage.

The following table lists the effects of the enzyme treatment on mechanical fragility and hematocrit of the erythrocytes.

TABLE I.

Properties of human erythrocytes treated with MBA-α-amylase.

|  | Washed cells | Control -amylase % | MBA α-amylase |
|---|---|---|---|
| Mechanical fragility | 7.95 ± 0.22 | 2.18 ± 0.01 | 2.11 ± 0.05 |
| Hematocrit | 29.0 ± 0.0 | 30.0 ± 0.45 | 30.3 ± 0.6 |

Coupling the enzyme to the cells resulted in a decrease in the mechanical fragility and little change in the hematocrit. The decrease in mechanical fragility was observed before with erythrocytes coupled to p-mercuribenzoate and DTNB adducts of α-amylase (Chen and Richardson, 1974; 1974a, supra). The osmotic hemolysis of the MBA-α-amylase-treated cells and cells treated with control enzyme fell within the normal range for human erythrocytes. These data indicate no gross changes in the physical characteristics of the membranes of erythrocytes treated with the MBA-α-amylase conjugate.

Problems in enzyme therapy include the short biological half-lives, immunogenicity and toxicity of enzymes. We have demonstrated the validity of the concept of covalently linking enzymes to tissues by treating human erythrocytes with reactive enzyme derivatives in vitro. It would seem reasonable that enzyme derivatives containing reactive groups could be immobilized in vivo by direct parenteral administration of the reactive enzymes. Enzymes tightly bound to tissues might have longer biological half-lives and less immunogenicity or toxicity.

The general idea of coupling macromolecules to living cells in order to prolong their biological activity can be applied in other ways. For example, in the immunotherapy of cancer it is possible to immobilize antigens in the tumor mass by intratumor administration of "reactive" proteins. An immune response directed toward the coupled antigen should destroy the tumor cells. Furthermore, the immobilization of toxin derivatives or enzyme derivatives that generate toxic products in tumors as suggested by Parker, Bower, Aach and Philpott, (1973) Pharmacology and the Future of Man., Proc. 5th Int. Congr. Pharmacology 5, 411–419, may be a valuable adjunct in cancer therapy.

For example, a new group of therapeutic systems for cancer can be provided for use in immunotherapy. It will be possible to immunize a host animal bearing a tumor against an antigen such as Bovine Serum Albumen (BSA) and then immobilize reactive derivatized BSA in the tumor site by injecting directly into or near the tumor. The immune response to BSA destroys the tumor cells bearing the antigen. In addition, enzymes that generate toxic products, such as peroxides, can be derivatized for immobilization in vivo, in accordance with the practice of this invention, by injection in or near the tumor site. Enzymes immobilized on tissues may be immunogenic. Thus, advantage can be taken of this phenomenon in the immunotherapy of cancer. In this regard, it might be possible to enhance the immunogenicity of reactive macromolecules by the addition of dinitrophenyl or trinitrophenyl residues. A therapeutic system can be visualized whereby the tumor-bearing host is immunized with a potent immunogen. The same immunogen can be derivatized in accordance with the concepts of this invention to become reactive. Intratumor injection of the derivatized immunogen results in its reaction with the surface of tumor cells. The humoral and cellular response to the initial immunization becomes focused on the tumor cells containing the reactive antigen to destroy the tumor cells. Furthermore, there should be an additional response of the immune system of the host to the immunogen-tumor cell conjugate. This approach would obviate the hazards of metastasis implicit in the administration of derivatized tumor cells to a host.

The immobilization of macromolecules on tissues presents other opportunities in the therapy of cancer. If toxic or potentially toxic macromolecules could be localized on tumor cells, selective cytotoxicity might result. For example, toxins such as diphtheria toxin can be derivatized to yield reactive derivatives which could be localized in a tumor mass by direct injection or injection into the tumor's vascular supply. In addition to toxins, enzymes which generate toxic products might be localized in tumors for cytotoxic effects. For example, soybean lipoxygenase which peroxidizes triglycerides and fatty acids might be immobilized on the surface of tumor cells to peroxidize the membrane lipids and thus destroy the cells. Alternatively, lipoxygenase immobilized in tumor can form toxic lipid hydroperoxides from circulating lipids.

It is possible to achieve localized and selective cytotoxicity by employing reactive enzyme derivatives. The enzymes enumerated by Parker, Bower, Aach and Philpott, supra, can be derivatized in accordance with the concepts of this invention as described for L-asparaginase. An enzyme with cytotoxic potential, lipoxygenase of soybeans, is commercially available. The various isoenzymes of soybean lipoxygenase catalyze the peroxidation by molecular oxygen of triglycerides or fatty acids containing the cis, cis 1,4-pentadiene double bond system. Soybean lipoxygenase can be immobilized in tumor site by using reactive derivatives. The area can then be flooded with trilinolein or linoleic acid to generate lipophilic hydroperoxides and their degradation products which are highly toxic. Alternatively there may be sufficient endogenous substrate for lipoxygenase activity. Furthermore, it seems possible to immobilize a peroxide decomposing system, such as hemoglobin, in the tumor site to facilitate the generation of free radicals for tumor destruction.

Since lipoxygenase requires molecular oxygen, the concentration of oxygen in tumor tissue is important. The oxygen tension of tumors is variable from tumor to tumor and in different parts of the same tumor. For example, in a Jensen sarcoma the oxygen tension may be as high as 80 mm mercury at the vascular capsule and essentially zero in necrotic areas (15). Intermediate values range from 10 to 30 mm mercury. A mean value of 18 mm mercury has been found in tumors with an intercapillary distance less than 350 microns. Approximate concentrations of oxygen at 80 mm Hg, 30 mm Hg and 18 mm Hg are $1.1 \times 10^{-4}$M, $4 \times 10^{-5}$M and $2.4 \times 10^{-5}$M, respectively, (using a Bunsen Coefficient of 0.024). This is favorable for the reaction of lipoxygenase, with a Km for oxygen of $3 \times 10^{-5}$M. From these data it is evident that significant lipoxygenase activity could take place at the oxygen tensions in tumor tissue. Furthermore, it should be possible to increase the oxygen tension of tissues with hyperbaric oxygen.

Selective cytotoxicity based on differences in the enzymology of tumor and normal cells allows the development of chemotherapeutic systems on a rational basis. However, predictable qualitative differences in enzymes between normal and tumor cells are dubious at best, and the quantitative differences between cell types are difficult to utilize as a basis for selective cytotoxicity.

In the chemotherapy of cancer it should be possible to produce a site-direction for chemotherapy by immobilizing specific enzymes in vivo. For example, a phosphamidase from plants could be derivatized and immobilized in a given area of tissue. This would be followed by systemic administration of cyclophosphamide. This nitrogen mustard derivative should be selectively activated in the area of high phosphamidase activity.

Alternatively, glucose oxidase could be immobilized in the tumor tissue. Since cyclophosphamide is activated in hepatic microsomes by an oxidative mechanism, the hydrogen peroxide generated in the area of the tumor by glucose oxidase serve to selectively activate the cyclophosphamide in the tumor.

The general concept of coupling macromolecules to living cells in order to prolong their biological activity can be applied in other ways to tumor chemotherapy. A variety of adjuncts to therapy, such as antigenic molecules that would become localized in tumors, toxic molecules such as diphtheria toxin, and enzymes such as peroxide-generating oxidases, that can generate toxic molecules from circulating substrates. The localization of such activated molecules can be achieved in several ways. Infusion into the tumor blood supply is an available technique. Also, direct intratumor administration. Furthermore, the immobilization of activating enzymes such as phosphamidase in the tumor mass may allow the activation of latent alkylating activity of cyclophosphamide within the tumor.

The immobilization of enzymes in vivo using synthetic, reactive enzyme derivatives is a novel concept which has broad implications in therapy of a variety of diseases. Reactive enzyme derivatives can be extended to the treatment of hyperlipoproteinemia using lipoprotein lipase and lecithin-cholesterol acyl transferase. In addition, some genetic deficiency diseases might be amenable to treatment with appropriate enzyme derivatives. In this latter case, past therapeutic studies have involved the use of homologous human enzymes isolated from placenta. Placental enzyme derivatives that prolong their biological half-lives would be significant in extending the supply of this limited source of homologous human enzyme.

The above illustrates the concept of immobilizing macromolecules on cells. This concept can be of utility in fermentation technology where enzymes can be attached to microbial cells for the assimilation and fermentation of substrates not otherwise used. It is believed to have profound significance in the therapy of enzyme deficiency diseases, in cancer therapy and in the therapy of hyperlipoproteinemia where lipoprotein lipase and lecithin cholesterol acyl transferase could be immobilized in the vascular system to "clear" lipoproteins from blood. In this latter case, the activity of α-amylase immobilized on erythrocytes on the starch macromolecules indicates that the large molecules can be susceptible to the immobilized enzymes.

It will be apparent from the foregoing that I have provided a simple and efficient means whereby enzymes and other macromolecules and proteins can be immobilized in vivo or in vitro on tissues or in human erythrocytes or cells whereby the enzymatic activity is retained over considerably greater periods of time while also increasing the half-life as well as improving the immunologic and immunosuppressive effects of the enzyme and without interfering materially with the activity of the enzyme.

It will be understood that changes may be made in the details of materials and preparation without departing from the spirit of the invention as outlined in the following claims.

TABLE OF REFERENCES (1) S. Baechittel and M. D. Prager. Basis for Loss of Therapeutic Effectiveness of L-Asparaginase in Sensitized Mice. Cancer Res. 33, 1966 (1973).

(2) D. A. Rutter and H. E. Wade. The Influence of the Isoelectric Point of L-Asparaginzse upon its Persistence in the Blood. Br. J. Exp. Path. 52, 610 (1971).

(3) O. Wagner, E. Irion, A. Arens and K. Bauer. Partially Deaminated L-Asparaginase. Biochem. Biophys. Res. Comm. 37, 383 (1969).

(4) E. Irion, A. Arens, E. Rauenbusch, K. Bauer, O. Wagner, R. Bierling and J. Puetter. Medicinally Partially Amidated L-Asparaginase. Ger. Offen. 2,039,061 (1972).

(5) L. E. Hare and R. E. Handschumacher. Physical and Biological Properties of Acetamidino, $\beta$-Dimethylaminopropionamidino and Maleyl Asparaginase. Mol. Pharmacol. 9, 534 (1973).

(6) E. Irion, A. Arens, E. Rauenbusch, K. Bauer, O. Wagner, R. Bierling and J. Puetter. Partially Acylated L-Asparaginase. Ger. Offen. 1,807,303 (1970).

(7) E. Irion, A. Arens, E. Rauenbusch, K. Bauer, O. Wagner, R. Bierling and J. Puetter. Azo-L-Asparaginases. Ger. Offen. 1,963,358 (1971).

(8) H. H. Weetal. Insolubilized L-Asparaginase Implant. A Preliminary Report. J. Biomed. Mater. Res. 4, 597 (1970).

(9) T. L. Westman, J. H. Johnson and B. S. Wildi. Enzymically Active Adducts of Asparaginase and Maleic Anhydride Copolymers. Ger. Offen. 1,943,748 (1970).

(10) J. P. Allison, L. Davidson, A. Guterrez-Hartman and G. B. Kitto. Insolubilization of L-Asparaginase by Covalent Attachment to Nylon Tubing. Biochem. Biophys. Res. Comm. 47, 66 (1972).

(11) T. M. S. Chang. L-Asparaginase Immobilized within Semipermeable Microcapsules in vitro and in vivo Stability. Enzyme 14, 95 (1972/73).

(12) S. J. Updike. Genetic Engineering, Enzyme Immobilization and Transplantation. Amer. J. Pharm. Ed. 36, 718 (1972).

(13) T. M. S. Change. The in vivo Effects of Semipermeable Microcapsules Containing L-Asparaginase on 6C3HED Lymphosarcoma. Nature 229, 117 (1971).

(14) Radley, J. A. (1968). Starch and its derivatives. 4th Ed., p. 433. Chapman and Hall, London.

(15) D. B. Cater. "The Significance of Oxygen Tension Measurements in Tissues" in Oxygen Measurements in Blood and Tissues (Ed. by J. B. Payne and D. W. Hill). J. & A. Churchill, London, 1966, p. 155.

I claim:

1. A method for immobilizing an enzyme on tissue or erythrocytes comprising the steps of reacting the enzyme having nucleophilic groups selected from the group consisting of amino, carboxyl and tyrosine groups with a compound containing an electrophilic group selected from the group consisting of $\alpha, \beta$ unsaturated carbonyls, alkyl halides, and thiol to form an enzyme derivative, and then immobilizing the enzyme on the tissue or erythrocyte having nucleophilic groups selected from the group consisting of sulfhydryl, amino, imidazole, carboxylato and tyrosine groups by a coupling reaction between electrophilic groups of the derivative and nucleophilic groups in the tissue or erythrocyte.

2. The method as claimed in claim 1 in which the nucleophilic group with which the enzyme derivative is interbonded in the tissue or erythrocyte is a sulfhydryl group.

3. The method as claimed in claim 1 in which the coupling compound in one containing free functional groups selected from the group consisting of free carboxyl groups, free amino groups, free aromatic amino groups, isocyanate groups, imidoester groups, acylating and alkylating groups.

4. The method as claimed in claim 1 which includes the step of reacting the enzyme or compound with an activator selected from the group consisting of chloro formate, carbodiimides and isoxazolium salt, or nitrous acid for aromatic amino groups prior to reaction of the compound with the enzyme to form the derivative.

5. The method as claimed in claim 4 in which the isoxazolium salts react with the enzyme to form an enol ester derivative of the enzyme.

6. The method as claimed in claim 4 in which the activator is isoxazolium salt.

7. The method as claimed in claim 1 in which the enzyme derivative is formed by reaction of isobutyl-chloro formate as an activator.

8. The method as claimed in claim 4 in which the activator is Woodward's reagent K.

* * * * *